(12) United States Patent
Gidwani et al.

(10) Patent No.: US 6,464,988 B1
(45) Date of Patent: Oct. 15, 2002

(54) GLIPIZIDE-CYCLODEXTRIN INCLUSION COMPLEXES AND THEIR PHARMACEUTICAL COMPOSITION

(75) Inventors: Suresh Kumar Gidwani, Mumbai (IN); Purushottam Singnurkar, Mumbai (IN); Prashant Kumar Tewari, Mumbai (IN)

(73) Assignee: USV Limited, Mumbai (IN)

(*) Notice: Subject to any disclaimer, the term of this patent is extended or adjusted under 35 U.S.C. 154(b) by 6 days.

(21) Appl. No.: 09/852,141

(22) Filed: May 9, 2001

(51) Int. Cl.[7] .................................. A61K 9/00
(52) U.S. Cl. ................. 424/400; 424/489; 514/255.06; 544/406
(58) Field of Search ................ 424/400, 489; 514/255.06; 544/406

(56) References Cited

FOREIGN PATENT DOCUMENTS

| WO | WO9748385 A | 12/1997 |
| WO | WO9847491 A | 10/1998 |

OTHER PUBLICATIONS

Database Chemabs Online! Chemical Abstracts Service, Columbus Ohio, US; Sun, Gudding et al "Studies on the preparation and release characteristics of glipizide hydrophilic gel tablets" retrieved from STN Database accession No. 127:39651 CA XP002174622; Abstract; & Zhongguo Yaoke Daxue Xuebao (1996) 27(11), 661–664, xp001015743.

Primary Examiner—Jose' G. Dees
Assistant Examiner—Konata M. George
(74) Attorney, Agent, or Firm—Gibbons, Del Deo, Dolan, Griffinger & Vecchione

(57) ABSTRACT

Inclusion complexes of glipizide and a nonionic surfactant with cyclodextrin and cyclodextrin derivatives. A method of preparing the inclusion complexes of glipizide and a nonionic surfactant with cyclodextrin and cyclodextrin derivatives, by wetting cyclodextrin or a derivative thereof with a nonionic surfactant, and mixing the resulting mixture with glipizide. A pharmaceutical composition containing an inclusion complex of glipizide and a nonionic surfactant with cyclodextrin and cyclodextrin derivatives, in combination with pharmaceutically acceptable excipients.

19 Claims, 4 Drawing Sheets

DSC THERMOGRAM OF GLIPIZIDE:

DSC THERMOGRAM OF BETA CYCLODEXTRIN:

DSC THERMOGRAM OF PHYSICAL MIXTURE OF GLIPIZIDE WITH BETA CYCLODEXTRIN (1:2) :

DSC THERMOGRAM OF INCLUSION COMPLEX OF
GLIPIZIDE WITH BET CYCLODEXFRIN (EXAMPLE 1):

GLIPIZIDE-CYCLODEXTRIN INCLUSION COMPLEXES AND THEIR PHARMACEUTICAL COMPOSITION

BACKGROUND OF THE INVENTION

1. Field of the Invention

The present invention relates to inclusion complexes of glipizide with cyclodextrin in presence of a nonionic surfactant. The invention also discloses a method for preparing such inclusion complexes, as well as pharmaceutical compositions containing the inclusion complex, in combination with pharmaceutically acceptable excipients.

More particularly the invention relates to inclusion complexes of glipizide preferably micronised with cyclodextrin or a cyclodextrin derivative in the presence of a nonionic surfactant, and pharmaceutical compositions there of.

2. Related Art

Formula 1

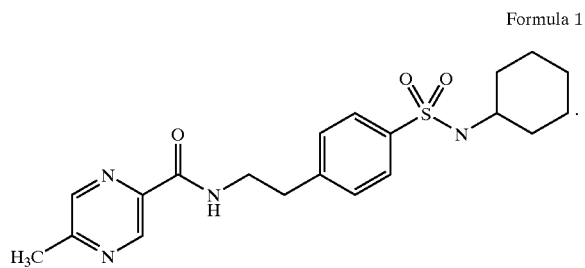

Glipizide of the formula 1 is an oral blood glucose lowering drug of the sulfonyl urea class. The chemical abstracts name of glipizide is 1-cyclohexyl -3-[[p-[2-(methylpyrazinecarboxamido)ethyl]phenyl]sulfonyl]urea. The molecular formula is $C_{21}H_{27}N_5O_4S$; and the molecular weight is 445.55. Glipizide is a whitish, odorless powder with pKa of 5.9. It is insoluble in water and alcohol but soluble in 0.1N NaOH.

Glipizide is a hydrophobic drug with poor aqueous solubility at room temperature. Also, glipizide being a weakly acidic drug, its aqueous solubility in the acidic pH of gastric juice is even less. Hence, after oral administration the drug is likely to be absorbed only in the lower path of gastrointestinal tract. This probably explains the protracted onset of biological effect of glipizide, although other theories are possible to explain this observation.

For rapid onset of action of glipizide during high blood glucose level conditions, high bioavailability is required which in turn is achieved by high aqueous solubility thereof. In order to achieve aqueous solubility and hence maximum absorption of the drug glipizide, so that it exhibits good pharmacological behavior, inclusion complexes of glipizide with cyclodextrin or cyclodextrin derivatives are prepared. Such rapid dissolving drug formulations of glipizide can be timed to meal taking events.

BRIEF SUMMARY OF THE INVENTION

One aspect of the invention is to provide an inclusion complex of glipizide and a nonionic surfactant with cyclodextrin, or a derivative thereof, which is safe for use as a pharmaceutical composition, renders the active drug glipizide highly soluble in physiological pH as well as in gastric fluid pH, and permits rapid dissolution of the active drug glipizide in physiological pH as well as in gastric fluid pH.

Another aspect of the invention is to provide a method for preparing an inclusion complex of glipizide and a nonionic surfactant with cyclodextrin, or a derivative thereof, which results in a product safe for use as a pharmaceutical composition. Such a method is simple, less time consuming than conventional techniques, efficient and economical, and which renders the active drug glipizide highly soluble in physiological pH as well as in gastric fluid pH and also permits rapid dissolution of the active drug glipizide in physiological pH as well as in gastric fluid pH.

Another aspect of the invention is to provide a method for preparing an inclusion complex of glipizide and a nonionic surfactant with cyclodextrin, or a derivative thereof which is suitable for manufacture of a product on commercial scale.

p Another aspect of the invention is to provide a pharmaceutical composition containing an inclusion complex of glipizide and a nonionic surfactant with cyclodextrin, or a derivative thereof, that is safe for use as a pharmaceutical, renders the active drug glipizide highly soluble in physiological pH as well as in gastric fluid pH, and permits rapid dissolution of the active drug glipizide in physiological pH as well as in gastric fluid pH.

Another aspect of the invention is to provide a method for the preparation of pharmaceutical compositions of an inclusion complex of glipizide and nonionic surfactant with cyclodextrin which results in a product safe for use as a pharmaceutical, renders the active drug glipizide highly soluble in physiological pH as well as in gastric fluid pH, and permits rapid dissolution of the active drug glipizide in physiological pH as well as in gastric fluid pH.

DETAILED DESCRIPTION OF THE INVENTION

Figure 1A:
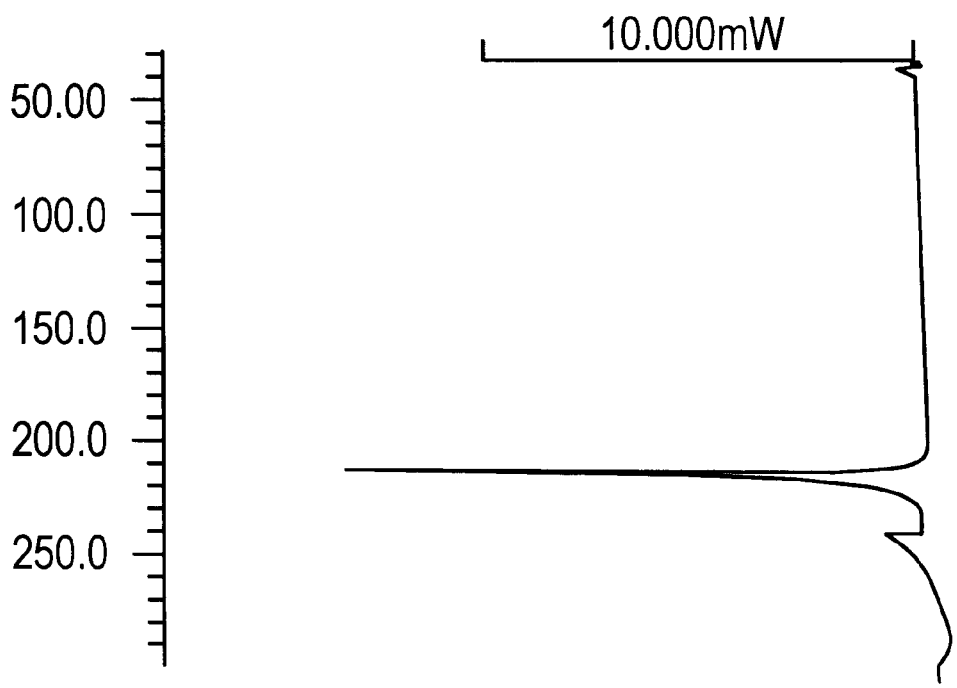
FIG. 1A is a DSC Thermogram of glipizide.
Figure 1B:
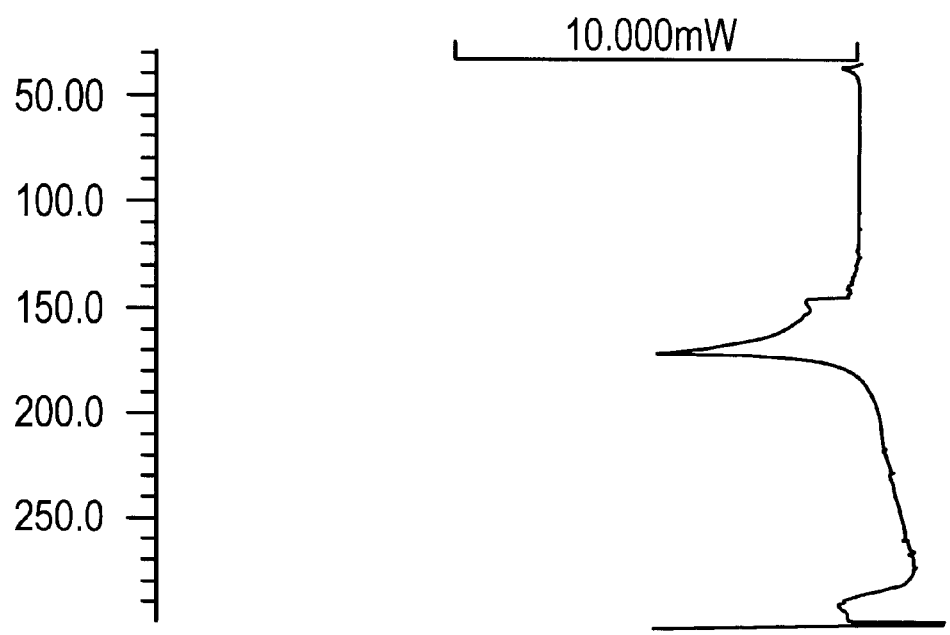
FIG. 1B is a DSC Thermogram of beta cyclodextrin.

According to the present invention there is provided an inclusion complex of 1-cyclohexyl-3-[[p-[2-(methylpyrazinecarboxamido) ethyl]phenyl]sulfonyl] urea, commonly known as glipizide of the formula 1.

Formula 1

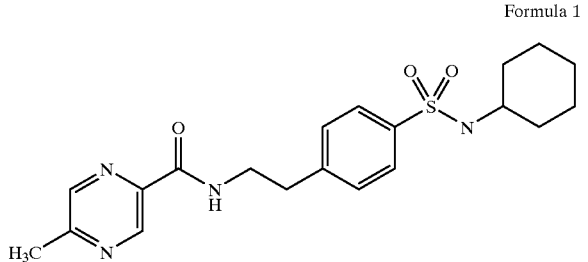

and a nonionic surfactant with cyclodextrin, or a derivative thereof, wherein glipizide is in micronised particle sizes of 1–40 μm and cyclodextrin, or a derivative thereof, is in particle sizes of 10–250 μm and the molar ratio of glipizide to cyclodextrin (or a derivative thereof) is 1:(1–4) and that of glipizide to the nonionic surfactant is 1:(0.1–1).

According to the invention there is also provided a method for the preparation of an inclusion complex of glipizide and a nonionic surfactant with cyclodextrin, or a derivative thereof, which comprises:

a) dissolving a nonionic surfactant in a pharmaceutically acceptable solvent such as water, acetone, and/or a C1–C4 aliphatic alcohol at room temperature.

b) wetting cyclodextrin or a cyclodextrin derivative of particle sizes 10–250 μm with the solution of nonionic surfactant to form a semisolid mixture.

c) mixing the semisolid mixture with glipizide of micronised particle sizes of 1–40 μm to form a mixed inclusion complex; and d) drying the mixed inclusion complex at 40–80° C., the molar ratio of glipizide to cyclodextrin or cyclodextrin derivative being 1:(1–4), the molar ratio of glipizide to nonionic surfactant being 1:(0.1–1); and the molar ratio of solvent to cyclodextrin or cyclodextrin derivative being 1:(3–6).

According to the present invention there is also provided a pharmaceutical composition containing an inclusion complex of glipizide and a nonionic surfactant with cyclodextrin, or a derivative thereof, in combination with pharmaceutically acceptable excipients, wherein the glipizide is in micronised particle sizes of 1.0 to 40 μm, the cyclodextrin or cyclodextrin derivative is in particle sizes of 10–250 μm and the molar ratio of glipizide to cyclodextrin or cyclodextrin derivative is 1:(1–4) and that of glipizide to nonionic surfactant is 1:(0.1–1).

According to the invention there is also provided a method for the preparation of a pharmaceutical composition containing an inclusion complex of glipizide and a nonionic surfactant with cyclodextrin or a derivative thereof, in combination with pharmaceutically acceptable excipients, wherein the glipizide is in micronised particle sizes of 1.0 to 40 μm, the cyclodextrin or cyclodextrin derivative is in particle sizes of 10–250 μm, the molar ratio of glipizide to cyclodextrin or cyclodextrin derivative is 1:(1–4) and that of glipizide to nonionic surfactant is 1:(0.1–1), which comprises mixing the inclusion complex with the excipients and if required converting it into desired form.

Preferably the particle sizes of glipizide may be 2–40 μm.

The cyclodextrin or cyclodextrin derivative of the inclusion complex may be alpha cyclodextrin, beta cyclodextrin, gamma cyclodextrin, or alkyl or hydroxy alkyl derivatives thereof. Preferably cyclodextrin may be beta cyclodextrin, gamma cyclodextrin, hydroxypropyl beta cyclodextrin and/or randomly methylated beta cyclodextrin.

The nonionic surfactant may be any pharmaceutically acceptable nonionic surfactant such as polyoxyl nonionic surfactant. Preferably polyoxyl-40-castor oil, polyoxyethylene-20-stearyl ether, polyoxyl-35-castor oil, polyoxyethylene-20-sorbitan monooleate, polyoxyethylene-20-sorbitan monolaurate is used as the nonionic surfactant.

Preferably water, isopropyl alcohol, or ethanol may be used as solvent.

The inclusion complex may be freeze dried or spray dried or dried by low temperature vacuum evaporation in a fluidized bed dryer or tray dryer. Preferably the shear mixed inclusion complex may be dried in tray dryer. Preferably drying is carried out at 40–60 degrees C.

The molar ratio of glipizide to cyclodextrin or cyclodextrin derivative may be preferably 1:(1–2). The molar ratio of glipizide to nonionic surfactant may be preferably 1:0.2. The molar ratio of solvent to cyclodextrin or cyclodextrin derivative may be preferably 1:4.5.

The excipients used may be lactose, microcrystalline cellulose, calcium carbonate, starch, colloidal silicone dioxide, sodium starch glycolate, magnesium stearate, polyvinyl pyrrolidone, and other excipients known in the art.

The pharmaceutical composition may be in the dosage form of a tablet or a capsule.

The inclusion complex of glipizide and nonionic surfactant with the cyclodextrin of the invention is unreported hitherto and is novel. According to the invention the glipizide is in micronised particle sizes of 1.0 to 40 μm for interaction with cyclodextrin or a derivative thereof. The micronised glipizide has increased surface area for better interaction with cyclodextrin or a cyclodextrin derivative. The solvent used is in considerably less quantity (solvent to cyclodextrin:: 1:3–6), and is sufficient to wet the cyclodextrin and result in a semisolid reaction mixture. The semisolid mixture of cyclodextrin and nonionic surfactant is amenable to shear mixing with glipizide because of which it has been possible to obtain an inclusion complex in which the glipizide is uniformly distributed and dispersed in the cyclodextrin matrix. The nonionic surfactant reduces the surface tension at the glipizide-cyclodextrin interface and also balances the hydrophilic-hydrophobic forces exerted at the surface of cyclodextrin particles to facilitate dispersion and distribution of the glipizide into the cyclodextrin matrix. Due to the above reasons, the inclusion complex formation is very effective and rapid. Because the nonionic surfactant in the inclusion complex reduces surface tension at the inclusion complex-physiological fluid interface and the glipizide is in micronised sizes, the drug is rendered highly soluble in physiological fluid and also bioavailable. The shear mixed inclusion complexes prepared by the method of the invention show rapid and high aqueous solubility of glipizide (95% dissolution at physiological pH of 6.8 within 15 minutes and 100% dissolution in within 30 minutes, 70% dissolution in neutral pH of water within 30 minutes and 45% dissolution in pH1.2 (gastric fluid) within 30 minutes).

The following experimental examples are illustrative of the invention but not limited of the scope thereof.

EXAMPLE 1

Polyoxyl-40-castor oil (10 gm) was dissolved in rectified spirit (115 ml). Beta cyclodextrin (260 gm, particle size 10–70 μm) was wetted with the solution of the nonionic surfactant (rectified spirit : beta cyclodextrin:: 1:2.26) and the reaction mixture was mixed in a suitable high shear mixer. To the semisolid mixture, glipizide (50 gm) milled to a particle size of 2 to 40 μm was added and mixed in high shear mixer for 1 hour (Glipizide:beta cyclodextrin:: 1:2, glipizide:polyoxyl-40-castor oil:: 1:0.2). The resulting semisolid mass was dried at 40–60° C. to obtain a solid inclusion complex of glipizide and polyoxyl-40-castor oil with beta cyclodextrin.

EXAMPLE 2

The procedure of Example 1 was followed using rectified spirit (200 ml) and beta cyclodextrin (500 gm) to obtain the inclusion complex (Glipizide:beta cyclodextrin:: 1:1, rectified spirit to beta cyclodextrin:: 1:1.3).

EXAMPLE 3

The procedure of Example 1 was followed using polyoxyethylene-20-stearyl ether (10 gm) as the nonionic surfactant to obtain the inclusion complex (Glipizide:polyoxyethylene-20-stearyl ether:: 1:0.2).

EXAMPLE 4

The procedure of Example 1 was followed using polyoxyl-30-castor oil (10 gm) as the nonionic surfactant to obtain the inclusion complex (Glipizide:polyoxyl-30-castor oil:: 1:0.2).

EXAMPLE 5

The procedure of Example 1 was followed using polyoxyethylene-20-sorbitan monooleate (10 gm) as the nonionic surfactant to obtain the inclusion complex (Glipizide:polyoxyethylene-20-sorbitan monooleate:: 1:0.2).

EXAMPLE 6

The procedure of Example 1 was followed using polyoxyethylene-20-sorbitan monolaurate (10 gm) as the nonionic surfactant to obtain the inclusion complex (Glipizide:polyoxyethylene-20-sorbitan monolaurate:: 1:0.2).

EXAMPLE 7

The procedure of Example 1 was followed using hydroxypropyl beta cyclodextrin (340 gm) as the cyclodextrin derivative to obtain the inclusion complex (Glipizide:hydroxypropyl beta cyclodextrin:: 1:2, rectified spirit to hydroxypropyl beta cyclodextrin:: 1:2.95).

EXAMPLE 8

The procedure of Example 1 was followed using rectified spirit (200 ml) as the solvent and hydroxypropyl beta cyclodextrin (169 gm) as the cyclodextrin derivative to obtain the inclusion complex (Glipizide: hydroxypropyl beta cyclodextrin:: 1:1, rectified spirit to hydroxypropyl beta cyclodextrin:: 1:2.95).

EXAMPLE 9

The procedure of Example 1 was followed using polyoxyl-35-castor oil (10 gm) as the nonionic surfactant and hydroxypropyl beta cyclodextrin (340 gm) as the cyclodextrin derivative to obtain the inclusion complex (Glipizide:hydroxypropyl beta cyclodextrin:: 1:2, glipizide:polyoxyl-35-castor oil:: 1:0.2, rectified spirit to hydroxypropyl beta cyclodextrin:: 1:2.95).

EXAMPLE 10

The procedure of Example 1 was followed using gamma cyclodextrin (291 gm) to obtain the inclusion complex (glipizide:gamma cyclodextrin:: 1:2, rectified spirit:gamma cyclodextrin:: 1:2.53).

EXAMPLE 11

The procedure of Example 1 was followed using randomly methylated beta cyclodextrin (299 gm) as the cyclodextrin derivative to obtain the inclusion complex (glipizide:gamma cyclodextrin:: 1:2, rectified spirit:gamma cyclodextrin:: 1:2.59).

EXAMPLE 12

The procedure of Example 1 was followed using isopropyl alcohol (115 ml) as the solvent to obtain the inclusion complex.

EXAMPLE 13

The procedure of Example 12 was followed using isopropyl alcohol (58 ml) as the solvent and beta cyclodextrin (130 gm) to obtain the inclusion complex (glipizide:beta cyclodextrin:: 1:1, isopropyl alcohol:beta cyclodextrin:: 1:2.24).

EXAMPLE 14

The procedure of Example 12 was followed using ethanol (115 ml) to obtain the inclusion complex.

EXAMPLE 15

The procedure of Example 12 was followed using hydroxypropyl beta cyclodextrin (340 gm) as the cyclodextrin derivative to obtain the inclusion complex (glipizide:hydroxypropyl beta cyclodextrin:: 1:2, isopropyl alcohol:hydroxypropyl beta cyclodextrin:: 1:2.95).

EXAMPLE 16

The procedure of Example 12 was followed using water (115 ml) in lieu of isopropyl alcohol, and beta cyclodextrin (260 gm) to obtain the inclusion complex(glipizide:beta cyclodextrin:: 1:2, water:beta cyclodextrin:: 1:2.26).

EXAMPLE 17

The procedure of Example 12 was followed using water (58 ml) in lieu of isopropyl alcohol, and beta cyclodextrin (130 gm) to obtain the inclusion complex (glipizide:beta cyclodextrin:: 1:1, water:beta cyclodextrin:: 1:2.26).

EXAMPLE 18

Pharmaceutical compositions in tablet form containing 5.0 mg, and 10 mg of glipizide were prepared by homogeneously mixing the inclusion complex of Example 1 with following additives, before being compressed into tablets.

| Ingredients | Contents in 5 mg Tablet | Contents in 10 mg Tablet |
| --- | --- | --- |
| Inclusion complex of Example 1. | 32 mg | 64 mg |
| Lactose granules | 104 mg | 208 mg |
| Starch | 5.1 mg | 10.2 mg |
| Microcrystalline cellulose | 15 mg | 30 mg |
| Sodium starch glycolate | 10 mg | 20 mg |
| Sodium lauryl sulfate | 5 mg | 10 mg |
| Crosspovidone | 10 mg | 20 mg |
| Aerosil ® | 1 mg | 2 mg |
| Magnesium stearate | 1 mg | 2 mg |

EXAMPLE 19

Pharmaceutical compositions in tablet form containing 5.0 mg, and 10 mg of glipizide were prepared by homogeneously mixing the inclusion complex of Example 1 with following additives, before being compressed into tablets.

| Ingredients | Contents in 5 mg Tablet | Contents in 10 mg Tablet |
| --- | --- | --- |
| Inclusion complex of Example 1. | ___ mg | ___ mg |
| Lactose granules | 104 mg | 208 mg |
| Starch | 5.1 mg | 10.2 mg |
| Microcrystalline cellulose | 15 mg | 30 mg |
| Sodium starch glycolate | 10 mg | 20 mg |
| Sodium lauryl sulfate | 5 mg | 10 mg |
| Crosspovidone | 10 mg | 20 mg |
| Aerosil ® | 1 mg | 2 mg |
| Magnesium stearate | 1 mg | 2 mg |

EXAMPLE 20

Pharmaceutical compositions in capsule form containing 5.0 mg, and 10 mg of glipizide were prepared by homogeneously mixing the inclusion complex of Example 1 with following additives, before being filled into hard gelatin capsule of size 2 for 5 mg glipizide capsule and size 1 for 10 mg glipizide capsule.

| Ingredients | Contents in 5 mg Tablet | Contents in 10 mg Tablet |
| --- | --- | --- |
| Inclusion complex of Example 1. | 32 mg | 64 mg |
| Lactose granules | 104 mg | 208 mg |
| Microcrystalline cellulose | 15 mg | 30 mg |
| Sodium starch glycolate | 10 mg | 20 mg |
| Sodium lauryl sulfate | 5 mg | 10 mg |
| Aerosil ® | 1 mg | 2 mg |
| Magnesium stearate | 1 mg | 2 mg |

EXAMPLE 21

50 gm of glipizide was mixed with 260 gm of beta cyclodextrin to obtain a physical mixture containing 5 mg of glipizide per 31 mg of mixture and 10 mg of glipizide per 62 mg of the mixture. (Glipizide:Beta cyclodextrin:: 1:2)

The inclusion complex of Example 1 was characterized as follows:

1. Quantitative Determination of Glipizide Form Inclusion Complex by HPLC:

The potency of the inclusion complex was calculated by HPLC with the following parameters.

| | |
| --- | --- |
| Mobile phase | Na Phosphate Buffer pH 6.0: Methanol (55:45) |
| Flow rate | 1 ml per min. |
| Temperature | Room temperature |
| Column | 15 cm × 3.9 mm, 5 $\mu$m with packing L1 |
| Detection wavelength | 225 nm |

The retention time of glipizide was found to be 12.5 minutes. 32 mg of the inclusion complex (Example 1) contained 5.01 mg of glipizide. This assay level proved that glipizide was uniformly dispersed through out the inclusion complex.

Figure 1C:
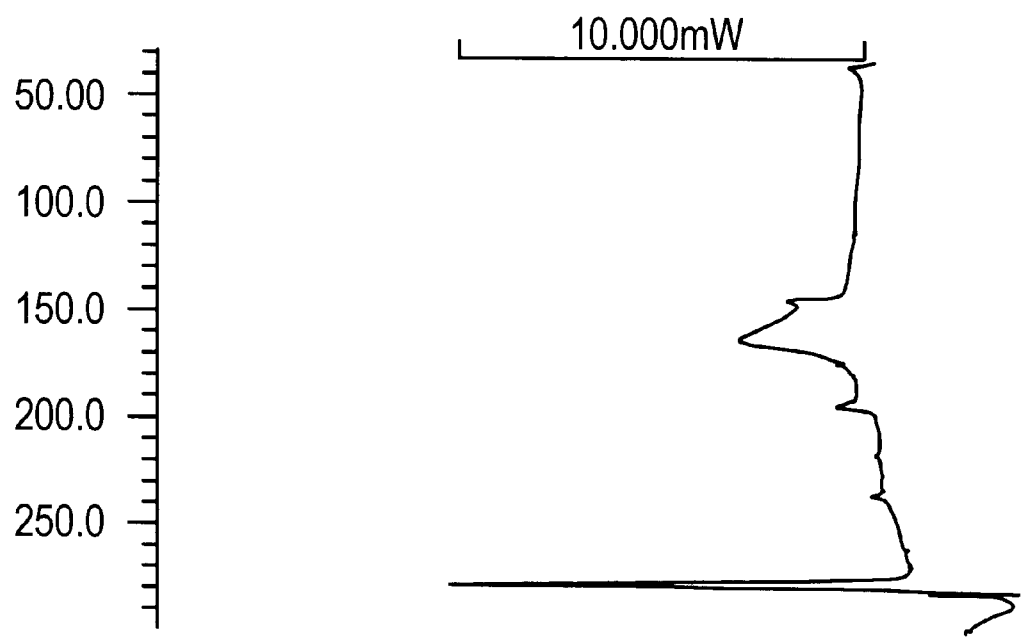
FIG. 1C is a DSC Thermogram of a physical mixture of glipizide with beta cyclodextrin (1:2).
Figure 1D:
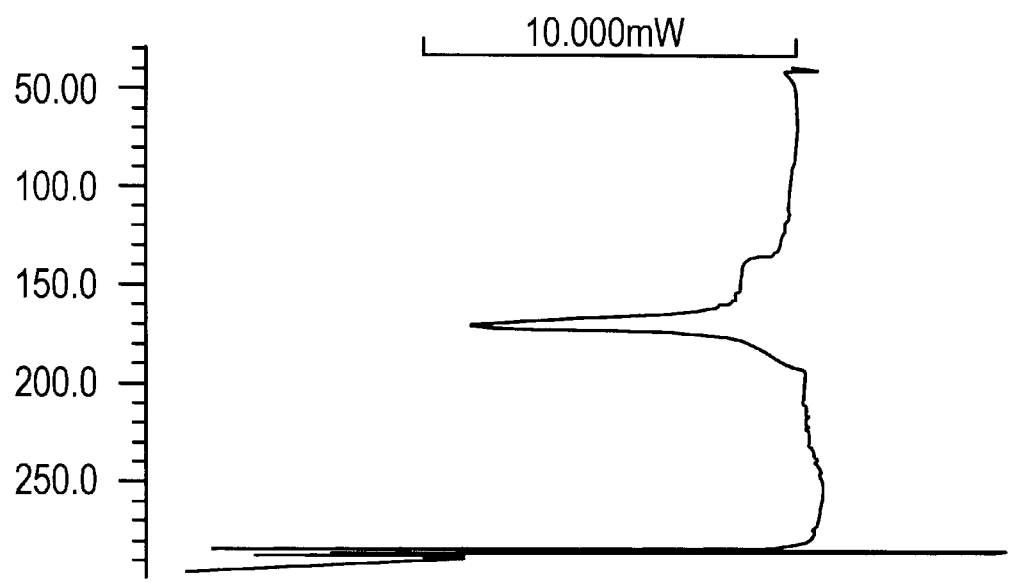
FIG. 1D is a DSC Thermogram of an inclusion complex of glipizide with beta cyclodextrin, as in Example 1.

2. Differential Scanning Calorimetry and NMR Study:

Thermograms of glipizide, beta cyclodextrin, a physical mixture of glipizide and beta cyclodextrin 1:2 and the glipizide-beta cyclodextrin inclusion complex of the present invention are as shown in FIGS. 1A, 1B, 1C, and 1D respectively. The peak at 210° C. in FIG. 1A was due to the melting of glipizide. FIG. 2B shows an endothermic peak at 168.1° C. corresponding to beta cyclodextrin. The physical mixture showed endothermic peaks of both glipizide at 205° C. and beta cyclodextrin at 161.5° C. as seen in FIG. 1C. The inclusion complex showed disappearance of the glipizide peak as seen in FIG. 1D. Disappearance of the glipizide peak at 210° C. showed the formation of inclusion complex which is further evidenced by 2D NOESY NMR spectra using Bruker 600 Hz FTNMR.

3. In-vitro Dissolution Studies:

In-vitro dissolution studies of the glipizide inclusion complexes of the present invention and glipizide (micronised) at various physiological pH were as shown Table 1:

TABLE 1

| Sr No | Dissolution Medium | Volume of dissolution medium | Time (Mins) | #1 | #2 | #3 | #4 | #5 |
| --- | --- | --- | --- | --- | --- | --- | --- | --- |
| 1 | Phosphate Buffer pH 68 USP | 900 ml | 5 | 62–77 | 25–29 | 65–75 | 26–28 | 25–28 |
| | | | 15 | 99–107 | 58–67 | 98–101 | 57–65 | 55–62 |
| | | | 30 | 100–107 | 67–69 | 99–102 | 68–71 | 65–68 |
| 2 | Phosphate | 400 ml | 5 | 69–72 | 27–34 | 68–72 | 26–35 | 24–29 |

TABLE 1-continued

| Sr No | Dissolution Medium | Volume of dissolution medium | Time (Mins) | #1 | #2 | #3 | #4 | #5 |
|---|---|---|---|---|---|---|---|---|
|  | Buffer pH 6.8 USP |  | 15 | 99–103 | 64–71 | 98–100 | 65–72 | 64–69 |
|  |  |  | 30 | 100–102 | 66–68 | 100–101 | 65–68 | 65–67 |
| 3 | Phosphate Buffer pH 6.8 USP | 200 ml | 5 | 70–73 | 28–32 | 67–72 | 28–32 | 23–27 |
|  |  |  | 15 | 98–100 | 63–69 | 96–99 | 64–68 | 65–67 |
|  |  |  | 30 | 99–101 | 64–68 | 100–101 | 65–67 | 64–67 |
| 4 | Purified water pH 7.0 | 900 ml | 5 | 60–63 | 25–31 | 61–62 | 24–28 | 20–25 |
|  |  |  | 15 | 69–75 | 35–45 | 68–72 | 32–41 | 30–33 |
|  |  |  | 30 | 71–75 | 42–46 | 72–74 | 40–42 | 38–41 |
| 5 | Purified water pH 7.0 | 400 ml | 5 | 54–60 | 35–37 | 52–59 | 36–38 | 32–34 |
|  |  |  | 15 | 62–70 | 42–46 | 63–68 | 44–45 | 40–42 |
|  |  |  | 30 | 65–70 | 43–46 | 65–70 | 44–48 | 40–44 |
| 6 | Purified water pH 7.0 | 200 ml | 5 | 55–58 | 34–36 | 53–57 | 35–37 | 30–32 |
|  |  |  | 15 | 63–69 | 40–44 | 60–65 | 42–46 | 38–40 |
|  |  |  | 30 | 68–71 | 43–45 | 64–68 | 44–48 | 39–41 |
| 7 | 0.1N Hydrochloric acid | 900 ml | 5 | 35–40 | 16–19 | 34–39 | 15–18 | 16–18 |
|  |  |  | 15 | 40–43 | 24–26 | 39–43 | 24–26 | 22–26 |
|  |  |  | 30 | 44–47 | 24–32 | 43–46 | 25–28 | 24–27 |
| 8 | 0.1N Hydrochloric acid | 400 ml | 5 | 30–36 | 17–22 | 32–35 | 16–18 | 16–20 |
|  |  |  | 15 | 30–44 | 29–37 | 34–45 | 25–28 | 26–27 |
|  |  |  | 30 | 43–48 | 29–38 | 44–50 | 26–30 | 26–30 |
| 9 | 0.1N Hydrochloric acid | 200 ml | 5 | 31–33 | 16–20 | 30–35 | 15–17 | 14–18 |
|  |  |  | 15 | 35–38 | 30–33 | 38–41 | 24–27 | 23–24 |
|  |  |  | 30 | 44–47 | 32–34 | 46–50 | 30–31 | 23–26 |

1 = % release of glipizide from the glipizide inclusion complex of Example 1 containing 5 mg of Glipizide.
2 = % release of glipizide from the physical mixture of glipizide and cyclodextrin of Example 21 containing 5 mg of Glipizide.
3 = % release of glipizide from the glipizide inclusion complex of Example 1 containing 10 mg of Glipizide.
4 = % release of glipizide from the physical mixture of glipizide and cyclodextrin of Example 21 containing 10 mg of Glipizide.
5 = % release of glipizide from 10 mg glipizide raw material.

The results of #1, and #3, show that the glipizide inclusion complexes when prepared by the method of invention exhibit high in-vitro glipizide release at various physiological pH as compared to the physical mixture of glipizide with cyclodextrin, indicated by the results of #2 and #4.

The results of #1, and #3 when compared with that of #5 show that the in-vitro release of glipizide from glipizide raw material is much less as compared to that from the inclusion complex prepared by the method of invention.

In-vitro dissolution studies of the inclusion complex of the invention and that of commercially available preparation of glipizide were shown in Table 2.

TABLE 2

| Sr No | Dissolution Medium | Volume of dissolution medium | Time (Mins) | #1 | #2 | #3 | #4 |
|---|---|---|---|---|---|---|---|
| 1 | Phosphate Buffer pH 6.8 USP | 900 ml | 5 | 68–72 | 68–73 | 24–27 | 25–28 |
|  |  |  | 15 | 98–102 | 97–100 | 51–56 | 53–54 |
|  |  |  | 30 | 100–105 | 99–102 | 70–74 | 71–73 |
| 2 | Phosphate Buffer pH 6.8 USP | 400 ml | 5 | 70–73 | 66–68 | 20–24 | 22–24 |
|  |  |  | 15 | 96–99 | 96–99 | 60–64 | 63–64 |
|  |  |  | 30 | 100–102 | 97–98 | 68–71 | 66–69 |
| 3 | Phosphate Buffer pH 6.8 USP | 200 ml | 5 | 69–71 | 65–68 | 23–26 | 22–23 |
|  |  |  | 15 | 94–97 | 95–98 | 64–65 | 60–63 |
|  |  |  | 30 | 98–99 | 99–100 | 68–72 | 67–70 |
| 4 | Purified water pH 7 | 900 ml | 5 | 62–66 | 60–63 | 22–25 | 22–24 |
|  |  |  | 15 | 70–76 | 68–70 | 29–32 | 30–32 |
|  |  |  | 30 | 74–78 | 72–74 | 38–42 | 38–40 |
| 5 | Purified water pH 7 | 400 ml | 5 | 58–61 | 54–56 | 31–34 | 31–35 |
|  |  |  | 15 | 64–70 | 62–68 | 40–44 | 39–42 |
|  |  |  | 30 | 68–70 | 67–71 | 40–44 | 42–44 |
| 6 | Purified water pH 7 | 200 ml | 5 | 57–59 | 52–56 | 28–32 | 29–33 |
|  |  |  | 15 | 65–68 | 60–65 | 36–38 | 35–38 |
|  |  |  | 30 | 66–69 | 68–70 | 37–40 | 36–38 |
| 7 | 0.1N Hydrochloric acid | 900 ml | 5 | 38–42 | 38–40 | 15–18 | 14–17 |
|  |  |  | 15 | 43–44 | 40–44 | 20–23 | 16–20 |
|  |  |  | 30 | 45–48 | 44–45 | 22–25 | 18–20 |

TABLE 2-continued

| Sr No | Dissolution Medium | Volume of dissolution medium | Time (Mins) | #1 | #2 | #3 | #4 |
|---|---|---|---|---|---|---|---|
| 8 | 0.1N Hydrochloric acid | 400 ml | 5 | 35–38 | 36–40 | 15–18 | 16–19 |
| | | | 15 | 39–42 | 38–42 | 22–25 | 21–24 |
| | | | 30 | 40–45 | 45–51 | 25–28 | 22–30 |
| 9 | 0.1N Hydrochloric acid | 200 ml | 5 | 32–37 | 33–35 | 13–16 | 14–16 |
| | | | 15 | 36–40 | 36–38 | 14–17 | 15–18 |
| | | | 30 | 38–40 | 40–42 | 14–18 | 16–18 |

1 = % release of glipizide from the glipizide inclusion complex of Example 18 containing 5 mg of Glipizide.
2 = % release of glipizide from the glipizide inclusion complex of Example 18 containing 10 mg of Glipizide.
3 = % release of glipizide from Glucotrol ® Tablet 5 mg (Pfizer Inc)
4 = % release of glipizide from Glucotrol ® Tablet 10 mg (Pfizer Inc)

We claim:

1. An inclusion complex of glipizide, that is, 1-cyclohexyl-3-[[p-[2-methyl pyrazine carboxamido) ethyl] phenyl]sulfonyl] urea, of the following formula Formula 1

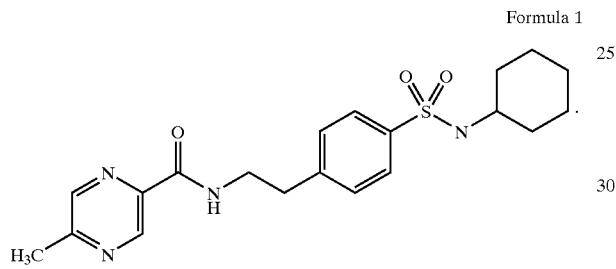

and a nonionic surfactant with a cyclodextrin or a cyclodextrin derivative, in combination with at least one pharmaceutically acceptable excipient, wherein the glipizide is in micronised particle sizes of 1.0 to 40 μm and the cyclodextrin or cyclodextrin derivative is in particle sizes of 10–250 μm and the molar ratio of glipizide to cyclodextrin or the cyclodextrin derivative is 1:(1–4) and that of glipizide to the nonionic surfactant is 1:(0.1–1.0).

2. The inclusion complex as claimed in claim 1, wherein the glipizide is in micronised particle sizes of 2–40 μm.

3. The inclusion complex as claimed in claim 1, wherein the cyclodextrin or cyclodextrin derivative is selected from a group consisting of is beta cyclodextrin, gamma cyclodextrin, hydroxypropyl beta cyclodextrin and randomly methylated beta cyclodextrin.

4. The inclusion complex as claimed in claim 1, wherein the nonionic surfactant is selected from a group consisting of polyoxyl-40-castor oil, polyoxyl-35-castor oil, polyoxyethylene-20-stearyl ether, polyoxyethylene-20-sorbitan monooleate or polyoxyethylene-20-sorbitan monolaurate.

5. The inclusion complex as claimed in claim 1, wherein the molar ratio of glipizide to cyclodextrin or cyclodextrin derivative is 1:(1–2).

6. The inclusion complex as claimed in claim 1, wherein the molar ratio of glipizide to the nonionic surfactant is 1:(0.1–0.2).

7. A method for preparing an inclusion complex of glipizide and a nonionic surfactant with a cyclodextrin or a cyclodextrin derivative, which comprises a) dissolving the nonionic surfactant in a pharmaceutically acceptable solvent at room temperature to obtain a solution.

b) wetting the cyclodextrin or cyclodextrin derivative of particle sizes 10–250 μm with the solution of nonionic surfactant to obtain a semisolid mixture.

c) mixing the semisolid mixture with glipizide of micronised particle sizes of 01–40 μm to form a mixed inclusion complex; and d) drying the mixed inclusion complex at 40–80° C., a molar ratio of glipizide to cyclodextrin or cyclodextrin derivative being 1:(1–4), a molar ratio of glipizide to nonionic surfactant being 1:(0.1–1); and a molar ratio of solvent to cyclodextrin or cyclodextrin derivative being 1:(3–6).

8. A method as claimed in claim 7, wherein the glipizide is in micronised particle sizes of 2–40 μm.

9. A method as claimed in claim 7, wherein the nonionic surfactant is selected from a group consisting of polyoxyl-40-castor oil, polyoxyl-35-castor oil, polyoxyethylene-20-stearyl ether, polyoxyethylene-20-sorbitan monooleate and polyoxyethylene-20-sorbitan monolaurate.

10. A method as claimed in claim 7, wherein the solvent is selected from a group consisting of water, rectified spirit, ethanol and isopropyl alcohol.

11. A method as claimed in claim 7, wherein the cyclodextrin or cyclodextrin derivative is selected from a group consisting of beta cyclodextrin, gamma cyclodextrin, hydroxypropyl beta cyclodextrin or randomly methylated beta cyclodextrin.

12. A method as claimed in claim 7, wherein a molar ratio of glipizide to cyclodextrin is 1:(1–2).

13. A method as claimed in claim 7, wherein a molar ratio of glipizide to the nonionic surfactant is 1:(0.1–0.2).

14. A pharmaceutical composition containing an inclusion complex of glipizide and a nonionic surfactant with a cyclodextrin or a cyclodextrin derivative, in combination with one or more pharmaceutically acceptable excipients, wherein the glipizide is in micronised particle sizes of 1.0 to 40 μm and the cyclodextrin or cyclodextrin derivative is in particle sizes of 10–250 μm and a molar ratio of glipizide to cyclodextrin or cyclodextrin derivative is 1:(1–4) and a molar ratio of glipizide to nonionic surfactant is 1:(0.1–1.0).

15. A pharmaceutical composition as claimed in claim 14, wherein the glipizide is in micronised particle sizes of 2–40 μm.

16. A pharmaceutical composition as claimed in claim 14, wherein the cyclodextrin or cyclodextrin derivative is selected from a group consisting of beta cyclodextrin, gamma cyclodextrin, hydroxypropyl beta cyclodextrin and randomly methylated beta cyclodextrin.

17. A pharmaceutical composition as claimed in claim 14, wherein the nonionic surfactant is selected from a group consisting of polyoxyl-40-castor oil, polyoxyl-35-castor oil, polyoxyethylene-20-stearyl ether, polyoxyethylene-20-sorbitan monooleate or polyoxyethylene-20-sorbitan monolaurate.

18. A pharmaceutical composition as claimed in claim 14, wherein the molar ratio of glipizide to cyclodextrin is 1:(1–2).

19. A pharmaceutical composition as claimed in claim 14, wherein the molar ratio of glipizide to nonionic surfactant is 1:(0.1–0.2).

* * * * *